United States Patent [19]

Paustian et al.

[11] 3,931,243

[45] Jan. 6, 1976

[54] PRODUCTION OF PHTHALIC ANHYDRIDE

[75] Inventors: John E. Paustian, Whippany; Abraham P. Gelbein, Plainfield, both of N.J.

[73] Assignee: The Lummus Company, Bloomfield, N.J.

[22] Filed: Jan. 28, 1974

[21] Appl. No.: 436,861

Related U.S. Application Data

[63] Continuation-in-part of Ser. No. 372,047, June 21, 1973.

[52] U.S. Cl. ........ 260/346.7; 260/346.3; 260/346.4; 260/346.8
[51] Int. Cl.² .................................. C07D 307/89
[58] Field of Search ........ 260/346.7, 346.3, 346.8 R

[56] References Cited
UNITED STATES PATENTS

| | | | |
|---|---|---|---|
| 2,478,464 | 8/1949 | Denton et al. | 260/465 |
| 2,499,055 | 2/1956 | Cosby et al. | 260/465 |
| 2,657,230 | 10/1953 | Rogers | 260/501.11 |
| 3,403,170 | 9/1968 | Corson et al. | 260/346.3 |

OTHER PUBLICATIONS

Houben–Weyl, Methoden Der Organischen Chemie, Stuttgart, Georg Thieme (1952) Vol. VIII Oxygen Compounds III p. 326 and 427–430.

*Primary Examiner*—Henry R. Jiles
*Assistant Examiner*—Bernard I. Dentz
*Attorney, Agent, or Firm*—Marn & Jangarathis

[57] ABSTRACT

Anhydrides of carboxylic acids, more particularly, of aromatic, naphthenic and saturated aliphatic acids having at least one pair of carboxyl groups attached to adjacent carbon atoms, can be prepared by thermal decomposition of amine salts of the acids, with removal of the amine. The amine salts may be produced by aqueous hydrolysis of the corresponding nitriles, imides, or amides in the presence of an amine, or by hydrolysis to the ammonium salts followed by conversion to the amine salt by stripping off ammonia in the presence of an amine.

8 Claims, No Drawings

PRODUCTION OF PHTHALIC ANHYDRIDE

RELATED APPLICATIONS

This application is a continuation-in-part of our application Ser. No. 372,047, filed June 21, 1973, entitled "Production of Amine Salts of Carboxylic Acids."

BACKGROUND AND DISCUSSION OF PRIOR ART

This invention relates to the production of anhydrides of aromatic naphthenic and saturated aliphatic carboxylic acids. More specifically, this invention relates to the production of anhydrides of polycarboxylic acids having at least one pair of carboxyl groups attached to adjacent carbon atoms of the molecule. The anhydride portion of the molecule therefore has the configuration

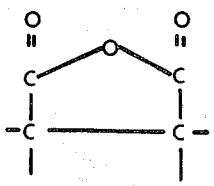

as compared with the structure of other anhydrides which may be generally represented as:

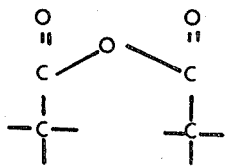

which are generally formed either by condensation of two molecules having the general formula R—COOH, (in which R may be hydrogen, or alkyl, cycloalkyl, aryl, heterocyclic, naphthenic, etc., with or without other substituents) or from a polycarboxylic acid having carboxyl groups attached to non-adjacent carbon atoms, e.g., terephthalic acid.

The predominant process for the production of anhydrides having at least one pair of carboxyl groups attached to adjacent carbon atoms is by air oxidation of a corresponding hydrocarbon or hydrocarbon derivative, such as an aldehyde, in the presence of a catalyst. For example, anhydrides of aromatic carboxylic acids such as phthalic, trimellitic and pyromellitic acids are commonly prepared by air oxidation of corresponding lower alkyl (e.g., methyl-, ethyl- and/or propyl-) substituted benzenes. In the case of phthalic anhydride the hydrocarbon is usually either naphthalene or orthoxylene; trimellitic acid is commercially prepared by air oxidation of pseudocumene and pyromellitic acid from durene. Similarly, anhydrides of aliphatic carboxylic acids of this type may also be prepared from corresponding hydrocarbons or derivatives thereof.

A second method of preparation of such anhydrides is by dehydration of the corresponding carboxylic acids.

Such processes are known to produce significant amounts of oxidized by-products, such as aldehydes, other carboxylic acids, ketones, etc. In some cases, the presence of such by-products may not be greatly disadvantageous to the process, because the anhydride may not be required in great purity. However, in some cases the presence of significant amounts of by-products will derogate from the suitability of the anhydride for the particular end use. For example, in the preparation of polyesters or polyamides from the anhydrides, the presence of impurities in significant amounts can interfere with the formation of appropriate polymer chains or result in cross-linking. Additionally, such by-products may give the polymers an undesirable color and/or other undesirable properties. For example, phthalic anhydride, when produced by the oxidation of orthoxylene, will contain small but significant amounts of partly oxidized compounds such as ortho-toluic acid and phthalide and over-oxidized compounds such as maleic anhydride and benzoic acid. Removal of such impurities is an expensive process, even though they may be present in quite small amounts, often less than 1 percent.

Purification of phthalic anhydride generally requires heating to polymerize some of the impurities and several distillation steps to separate and recover the anhydride.

More recently it has been found that aromatic carboxylic acids can be prepared by conversion of the corresponding hydrocarbons to nitriles, followed by conversion of the nitriles to acids, e.g., by hydrolysis. The hydrolysis may be performed with or without the aid of a catalyst, and with stripping of the ammonia from the hydrolysis product, and results in the formation of ammonium salts of the acids. Anhydrides of acids having at least one pair of carboxyl groups attached to adjacent carbon atoms, e.g., phthalic, trimellitic and pyromellitic can be obtained by thermal decomposition of the ammonium salt(s). However, such processes also tend to produce substantial amounts of the corresponding imide, and subsequent purification of the anhydride will be required to eliminate this and other nitrogen-containing by-products such as intermediate hydrolysis products, which could interfere with the production of polyesters or polyamides.

The carboxylic acids and/or their ammonium salts may also be produced by hydrolysis of corresponding amides or imides.

It is an object of the present invention to produce anhydrides of aromatic, naphthenic and saturated aliphatic carboxylic acids without requiring production of the acid as an intermediate compound. More specifically, it is an object of the present invention to produce anhydrides of aromatic, naphthenic and saturated aliphatic polycarboxylic acids having at least one pair of carboxyl groups attached to adjacent carbon atoms. A second object of this invention is to produce anhydrides of such carboxylic acids free from the presence of undesirable oxidation by-products. Another object of the present invention is to provide anhydrides of such carboxylic acids suitable for use in the production of polyesters, polyamides, and other polymeric compounds. Yet another object of the present invention is the production of anhydrides of such aromatic and aliphatic carboxylic acids from the corresponding nitriles. A further object of the present invention is to produce such anhydrides from amine salts of the corresponding acids. A still further object of the present invention is to produce such anhydrides from the nitriles of the corresponding acids, with the production of the amine salt of the acid as an intermediate, and without requiring separation of the amine salts from the hydrolysis products.

SUMMARY OF THE INVENTION

In one aspect, the invention described herein comprises the production of anhydrides of aromatic, naphthenic and saturated aliphatic polycarboxylic acids having at least one pair of carboxyl groups attached to adjacent carbon atoms from the carresponding amine salts by thermal decomposition of the salts, either per se or in aqueous solution.

In another aspect, the invention described herein comprises the production of anhydrides of such acids from the corresponding nitriles, imides and/or amides by aqueous hydrolysis and conversion of the hydrolysis products to the corresponding amine salts, or aqueous solutions thereof, followed by thermal decomposition of the salts, either per se or in aqueous solution.

In yet another aspect, the invention described herein comprises the production of anhydrides of such carboxylic acids from the corresponding nitriles, imides and/or amides by aqueous hydrolysis in the presence of an amine, with continuous stripping to remove evolved ammonia to produce the corresponding amine salts, or aqueous solutions thereof, followed by thermal decomposition of the amine salts to the anhydride, with continuous removal of amine. In yet a fourth aspect, the invention comprises the production of anhydrides of such carboxylic acids from corresponding hydrocarbons without the production of undesirable oxidation by-products by first contacting the hydrocarbon with ammonia and a catalyst, optionally in the presence of free oxygen to form the corresponding nitrile or mixture of nitrile and imide, and/or amides, followed by hydrolysis in the presence of an amine, as above, to produce the amine salt, with subsequent thermal decomposition of the amine salt and removal of the amine to produce the anhydride.

DETAILED DESCRIPTION AND PREFERRED EMBODIMENTS

For convenience, the detailed description of the process of the present invention will be described in terms of the production of phthalic anhydride via the di(-trimethylammonium) salt of phthalic acid, which has been prepared from phthalonitrile, phthalimide or a mixture of the two by hydrolysis in the presence of trimethylamine. As further illustrated below, however, the process is applicable to anhydrides of other aromatic, naphthenic and saturated aliphatic polycarboxylic acids having at least one pair of carboxyl groups attached to adjacent carbon atoms, and their preparation from amine salts of the corresponding acids, whether obtained by hydrolysis as above, or in any other manner.

Processes for preparing nitriles by catalytic reaction of corresponding hydrocarbons with ammonia and oxygen are well known in the art. Generally speaking, such processes involve the use of free oxygen (usually as air), in which case the process is usually referred to as ammoxidation. Alternatively, as disclosed in U.S. application Ser. No. 147,159, filed May 26, 1971, copending herewith, and assigned to the assignee hereof, this type of process can also be carried out in the substantial absence of free oxygen, in the presence of a catalyst which contains oxygen combined therein, and which is believed to both catalyze the reaction and supply the oxygen, the catalyst being at least partially reduced in the process. Such a process may be referred to as ammonolysis.

Such reaction (in the case of methyl-substituted benzenes) produces primarily the nitrile corresponding to the methylbenzene, or in the case of polymethylbenzenes, a mixture of the desired polynitrile and other nitriles. In the case of methylbenzenes having one or more pairs of methyl groups in the ortho position with respect to each other, the reaction products will contain some amount of the corresponding cyclic imide (e.g., phthalimide).

The reaction, in general, for compounds which do not have two methyl groups in the ortho position on the aromatic ring can be represented as:

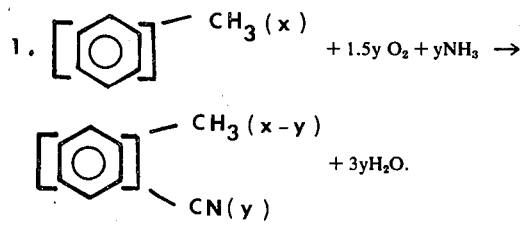

In the case of aromatic compounds having one or more pairs of methyl groups in the ortho position on the aromatic ring, however, additional reactions are also possible. In the case of ortho-xylene, for instance, the following reactions may occur:

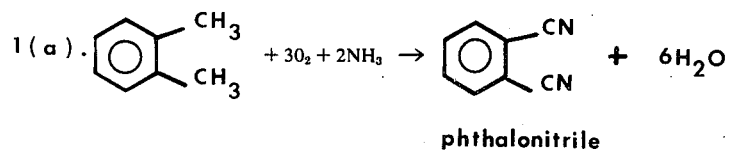

phthalonitrile

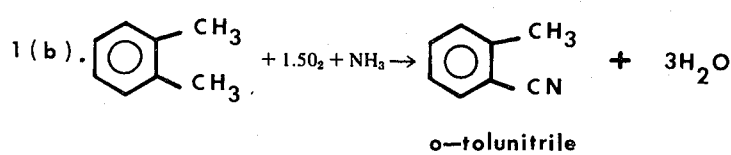

o—tolunitrile

1(c). 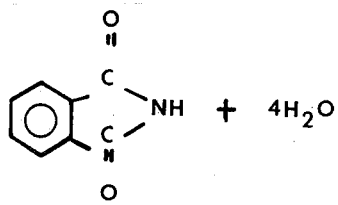

phthalimide

Generally, in the reaction of ortho-xylene to produce phthalonitrile, all three reactions will occur to some extent, and the product will contain some o-tolunitrile and phthalimide.

In commercial practice today, phthalimide is regarded as an undesirable by-product or contaminant and steps are taken to prevent its formation or separate it from the desired nitrile. As will be pointed out below, however, the presence of phthalimide will not be detrimental in the utilization of the present invention, as it will be converted to the desired amine salt. Phthalimide may in fact be considered desirable in that it is hydrolyzed even more readily than the nitrile.

Analogously, the reaction of other aromatic compounds having ortho-dimethyl (or other lower-alkyl) configurations, such as durene, pseudocumene and ortho-dimethylnaphthalenes, with ammonia and oxygen will result in the production of some imide, which can be converted to the desired amine salt by the process of our invention without necessitating its separation from the desired nitrile.

Other nitriles, such as o-tolunitrile, will also be hydrolyzed to amine salts of their corresponding carboxylic acids. Separation of these nitriles or the amine salts or other derivatives of the acid may be necessary to avoid contamination of the final product.

The ammoxidation or ammonolysis reactions are generally conducted at temperatures of 600° to 1000°F, total pressures of 1 to 5 atmospheres, residence times of 1 to 30 seconds and feed compositions containing from stoichiometric amounts of reactants to large excesses of $O_2$ and $NH_3$ with or without diluents.

The products of the ammoxidation or ammonolysis reaction are, according to the invention, then subjected to an aqueous hydrolysis step under pressure and at elevated temperatures, in the presence of an amine, which may be either a primary, secondary, or tertiary amine, preferably a tertiary amine, (as its use essentially precludes formation of imides in the subsequent processing steps, as pointed out hereinafter) with continuous removal of ammonia evolved, to convert the reaction products to the amine salt of the corresponding polycarboxylic acid and ammonia.

Alternatively, the conversion to the amine salt can be carried out in two steps: hydrolysis to form the ammonium salt followed by stripping of ammonia in the presence of amine.

The hydrolysis of the phthalonitrile-phthalimide mixture with trimethylamine proceeds according to the following reactions, depending on the feed:

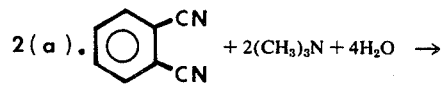

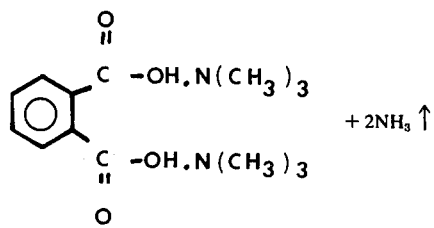

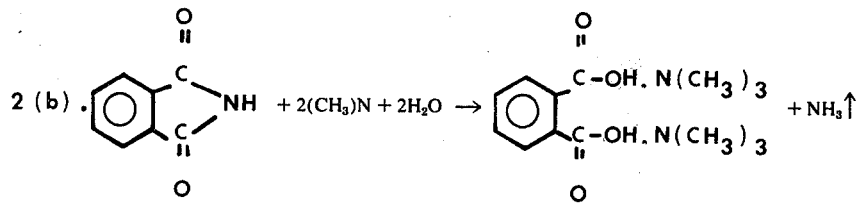

The hydrolysis is carried out at temperatures of between 150° and 500°F, preferably between 200° and 450°F, under autogenous pressure of the system. The ammonia evolved is removed from the reaction products, preferably by countercurrent stripping with steam or other suitable inert gas (e.g., helium, nitrogen, methane, paraffins, etc.). Ammonia must be reduced to low levels before subsequent decomposition of the amine salt as larger concentrations of ammonia may result in substantial imide formation during decomposition.

In one preferred embodiment, the hydrolysis is carried out in a continuous fashion, preferably in a vertically disposed reactor, with continuous introduction of reactants and withdrawal of products. Alternatively, the hydrolysis could be conducted as a batch process. In the first case, ammonia is preferably stripped by introducing the stripping gas into the hydrolysis reactor countercurrently to the flow of reactants, so that all operations can be carried out in one reactor. If a volatile amine is utilized, some will be stripped along with the ammonia and provision should be made for separation and recycling or refluxing the amine to the reactor. Preferably the amine, both fresh feed and recycle, is mixed with the stripping gas prior to its introduction into the reactor.

Alternatively, for most nitriles, the hydrolysis can be carried out to produce the corresponding ammonium salts and the reaction products can be continuously stripped in a second piece of apparatus. In a batch operation, stripping will generally be performed in a subsequent step, either in the same or another piece of apparatus.

As the hydrolysis reaction (reactions 2a and/or 2b) will be carried out in excess water and the amine salts are water-soluble, the products will remain in solution and the mixture will contain for example, hydroxyl, ammonium, and trimethylammonium ions, as depicted in the following reactions 3–5, as well as phthalate ions:

3. $(CH_3)_3N + H_2O \rightleftharpoons (CH_3)_3NHOH \rightleftharpoons [(CH_3)_3NH]^+ + [OH]^-$
4. $NH_3 + H_2O \rightleftharpoons NH_4OH \rightleftharpoons [NH_4]^+ + [OH]^-$ Overall, the reaction is:

5. $(CH_3)_3N + [NH_4]^+ \rightleftharpoons [(CH_3)_3NH]^+ + NH_3$

Analogous reactions take place for salts of other amines and other acids as this class of compounds is generally water-soluble, and the products of the reaction will, in general, be an aqueous solution containing carboxyl anions and alkyl substituted ammonium cations.

Since aliphatic amines are more basic than ammonia (for example the dissociation constant of ammonia is 4.75, that of trimethylamine is 4.20, and that of triethylamine 3.36) the equilibrium of reaction 5 will be shifted to the right and that of reaction 3 will be more to the right than that of reaction 4. The higher concentration of hydroxyl ions will therefore effect hydrolysis of the ammoxidation or ammonolysis reaction products more rapidly than will ammonium hydroxide (i.e., ammonia) alone. In addition, separation of ammonia for recycle to the ammoxidation or ammonolysis reactor is facilitated (reaction 5).

One advantage of the present invention is that the anhydrides may be produced from the reaction products of the amine hydrolysis-ammonia stripping step without actual recovery of the amine salts from the aqueous solution. However, it may be in some cases advantageous to recover these salts by evaporation, fractional crystallization or other conventional methods to recover the amine salts as solids, for example, if these salts are to be stored or shipped or further treated in another location or at a subsequent time.

The amine salt, either in the form of the aqueous solution, or per se, is subjected to a thermal decomposition, with removal of the amine and any water present, to produce the anhydride of the corresponding carboxylic acid. The decomposition of di(trimethylammonium) phthalate, for instance, proceeds according to the reaction:

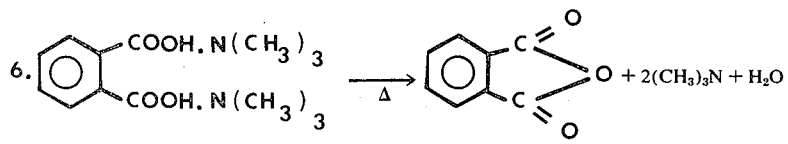

The thermal decomposition is conducted without added water, and with stripping of water already present, if the amine salt is in aqueous solution. The amine is also removed, i.e., by stripping, during the thermal decomposition, leaving the anhydride. Decomposition of the isolated amine salt may be conducted in any suitable fashion and the amine continuously removed during decomposition by stripping with an inert gas such as nitrogen or steam. Some of these salts have low melting points and may be in liquid or melt form at the decomposition temperature; the method of decomposition and equipment used therefor should be selected with this possibility in mind. Decomposition of aqueous solutions of amine salts may be performed by spray drying or other conventional means, with continuous removal of amine and water by stripping with a suitable inert gas such as nitrogen or steam. More preferably the decomposition of the aqueous amine salt solution is accomplished by heating in an inert liquid medium such as dodecane, ortho-xylene, mesitylene, pseudocumene, α-methylnaphthalene or adiponitrile, which functions as a heat transfer medium, together with stripping of the amine by evolved steam. The starting hydrocarbon material is most preferred as the inert liquid medium. If the decomposition is performed at the boiling point of the inert liquid, vapors of the liquid which evolve can be used as the stripping gas, either alone or together with an inert gas, such as steam or nitrogen. In general, the decomposition is conducted at temperatures of about 100°F to about 450°F. The rate of decomposition is rapid and hence the residence time for the decomposition is a function of the mass-transfer characteristics of the system. The recovered amine is preferably recycled to the hydrolysis step for use therein.

In general, the amine utilized in this process can be any amine which is preferably at least as basic as ammonia and has sufficient solubility in water under the hydrolysis conditions employed to ensure adequate hydroxyl ion concentration. In selecting the amine, consideration should be given to the possibilities of complications (e.g., side reactions or reactions between two amine molecules) which may occur in some situations when amines having additional functional groups are utilized. For example, depending on operating conditions, amines having functional groups such as ethers, halogen atoms, nitro groups or unsaturation, may undergo, respectively, cleavage, hydrolysis, thermal decomposition or polymerization, or addition reactions. Use of an alkanolamine may involve the possibility of an esterification reaction.

While it is possible to utilize primary, secondary or tertiary amines in this process, tertiary amines are highly preferred. Salts of primary or secondary amines may decompose on heating, with the formation of mono- or dialkylamides. Amine salts of acids having two carboxyl groups attached to adjacent carbon atoms, e.g., phthalic acid, tend to decompose even more readily than others, forming the corresponding N-alkylimide. Salts of tertiary amines do not form either amides or imides. However, depending on the reaction conditions and the desired anhydride, the amount of imide or amide formed when using primary or secondary amines may not be so large as to be detrimental to the use of the product anhydride in further processing. Additionally amides and imides may be recycled to the hydrolysis steps to be reconverted to amine salt. This can, however, increase the processing cost as compared to the use of a tertiary amine. Prevention of amide and/or imide formation is also assisted by ensuring that ammonia is removed prior to the decomposition step, e.g., by stripping from the hydrolysis mixture.

In general, low molecular weight tertiary aliphatic amines are preferred. Most preferred are amines such as trimethylamine, N,N,N',N'-tetramethylethylenediamine and N,N,N',N'-tetramethyl-1,3-propylenediamine. Other suitable tertiary amines are triethylamine, dimethylethylamine, diethylmethylamine, triethylenediamine, N,N,N',N'-tetramethyl-1,3- and 1,4-butanediamines and quinuclidine. Other aliphatic amines which may be considered for use are e.g., methylamine, dimethylamine, ethylamine, diethylamine and homologous compounds.

Aromatic amines with an alkyl group between the amine group and aromatic group would also be useful. Typical examples are benzylamine and xylylamine and N-substituted analogues thereof. Pyridine and some of its methyl-substituted derivatives such as the picolines and lutidines should also be effective, given sufficient time and temperature, because of their solubility in water. Even though they are less basic than ammonia, ammonia is much more volatile and can be stripped off as it forms.

The process of our invention, in addition to being suitable for the production of phthalic anhydride, is also suitable for the production of other such carboxylic acid anhydrides. For instance, the process may be utilized to produce anhydrides of aromatic polycarboxylic acids such as trimellitic, pyromellitic, mellophanic, hemimellitic, prehnitic, mellitic, 1,2-naphthalenedicarboxylic and 2,3-naphthalenedicarboxylic acids. Anhydrides of heterocyclic acids such as quinolinic and cinchomeronic may be produced, as may anhydrides of non-aromatic cyclic hydrocarbon, i.e., naphthenic, carboxylic acids such as tetrahydrophthalic, 1,1-dimethyl-2,3-cyclopropanedicarboxylic and cis-1,2-cyclopentanedicarboxylic.

Anhydrides of aliphatic carboxylic acids which may be produced by this process include succinic acid and its homologues, e.g., pyrotartaric acid.

As mentioned previously, imides can also be hydrolyzed to the amine salt of the corresponding carboxylic acids by the present process, either as the sole feed or in a mixture with the nitrile. This becomes particularly important in the production of anhydrides of certain acids, for example, phthalic acid, since the present commerical processes for production of phthalonitrile generally also produce phthalimide as well (see equation 1c), sometimes in substantial quantities. Ordinarily the phthalimide must be separated from the nitrile before the nitrile can be further used. In the present invention, however, a mixture of nitrile and imide is quite satisfactory as a hydrolysis feed.

Intermediate hydrolysis products of the nitrile such as amides, including mixed cyano-amides (e.g., o-cyanobenzamide) and other similar compounds having a mixture of substituents, e.g., from recycled streams, may also comprise the hydrolysis feed, or be included in a feed comprising a nitrile, imide, or mixture thereof.

The nature of the invention may be further illustrated by the following examples, without however, being limited thereby.

EXAMPLE I

A 43 weight % solution of bis(trimethylammonium) phthalate was added dropwise to refluxing dodecane (211°C). Trimethylamine and water were stripped from the reaction mixture. White needles were filtered from the dodecane after cooling which assayed as substantially pure phthalic anhydride by titration with standard base.

EXAMPLE II 66.5g of 43% bis(trimethylammonium) phthalate was dropped into 200 ml of refluxing (143°C) o-xylene which had previously been saturated with phthalic anhydride at room temperature. The addition took 88 minutes; stripping was continued for an additional 119 minutes. Amine recovery from the exit gas was 86% with another 7% from undecomposed salt remaining in the xylene. On cooling to room temperature, white crystals were filtered which were identified by infrared analysis as phthalic anhydride, the weight of which represented 96.6% of theory based upon the amine salt charged. This solid contained only 46 ppm nitrogen as analyzed by Kjeldahl digestion.

It was also noted that once phthalic anhydride solubility in the hot o-xylene was exceeded, the product separated as a fused, lower layer from which it could be drawn off continuously during the salt decomposition.

EXAMPLE III

A 40g sample of crude, xylene-wet phthalonitrile obtained from the ammonolysis of o-xylene and 172g of 25% aqueous trimethylamine were charged to an autoclave and heated for 4 hours at 300°F. At this temperature, the pressure was 240 psig. After cooling, the reaction mixture was a clear, homogeneous solution, light yellow, with a xylene upper layer. The xylene was separated and the bottom layer heated to approx. 125°F, then stripped with trimethylamine vapor at atmospheric pressure for 1.5 hours. Ammonia was removed from the hydrolyzate as shown by GC analysis of the evolved vapors.

At this point, the solution was recharged to the autoclave and reheated for an additional 4 hours at 300°F and its autogenous pressure.

After cooling, the solution was re-stripped with trimethylamine vapor as described above until the ammonia concentration in vapor was less than 1 part per 1000 of amine.

The remaining solution was added to 500 ml of o-xylene in a glsss flask fitted with a trap and condenser, then brought to reflux. Initially, the xylene-water azeotrope was removed; separation of water/amine and xylene was effected in the trap and the xylene returned. Reflux was continued until the boiling point of the xylene was reached and amine/water evolution had essentially ceased. Cooling of the flask contents resulted in crystallization of a white solid which was phthalic anhydride by infrared analysis. Phthalimide was not present according to this analysis.

A portion of this solid was distilled under vacuum and an overhead fraction boiling at approx. 160°C and approx. 25 mm Hg was collected. The melting point of this material was the same as that of a pure, commercial phthalic anhydride.

Equivalents and other embodiments of the invention will be readily apparent to those skilled in the art. Consequently, the invention is not deemed to be limited to the specifics disclosed herein, but only as defined in the following claims.

We claim:

1. A process for producing phthalic anhydride, comprising:
   a. hydrolyzing a feed comprising phthalonitrile with an aqueous solution of a tertiary aliphatic amine at a temperature of from 150° to 500°F while removing evolved ammonia to produce the corresponding diamine salt of phthalic acid; and
   b. thermally decomposing said diamine salt of phthalic acid while continuously removing evolved amine to produce phthalic anhydride.

2. The process of claim 1 wherein the diamine salt is decomposed at temperatures of 100° to 450°F.

3. The process of claim 2 wherein diamine salt is decomposed in the form of an aqueous solution.

4. The process of claim 2 wherein the decomposition is effected by heating the aqueous solution in an inert liquid.

5. The process of claim 4 wherein the decomposition is effected at a temperature to effect volatization of the inert liquid which functions as a stripping gas.

6. The process of claim 2 wherein the feed in step (a) further contains phthalimide.

7. The process of claim 2 wherein the amine is trimethylamine.

8. The process of claim 2 wherein the amine is N,N,N',N'-tetramethylethylenediamine.

* * * * *